United States Patent [19]

Berthold

[11] 4,304,915

[45] Dec. 8, 1981

[54] 3-AMINOPROPOXYARYL DERIVATIVES, THEIR PREPARATION AND PHARMACEUTICAL COMPOSITIONS CONTAINING THEM

[75] Inventor: Richard Berthold, Bottmingen, Switzerland

[73] Assignee: Sandoz Ltd., Basel, Switzerland

[21] Appl. No.: 54,537

[22] Filed: Jul. 3, 1979

[30] Foreign Application Priority Data

| Jul. 3, 1978 | [CH] | Switzerland | 2240/78 |
| Jul. 3, 1978 | [CH] | Switzerland | 7235/78 |
| Jan. 18, 1979 | [CH] | Switzerland | 491/79 |
| Jan. 18, 1979 | [CH] | Switzerland | 496/79 |

[51] Int. Cl.$^3$ ........................................ C07D 401/14
[52] U.S. Cl. ........................ 546/201; 260/326.15; 544/316; 544/373; 546/273
[58] Field of Search .................. 544/373, 316; 260/326.15; 546/201, 273

[56] References Cited

U.S. PATENT DOCUMENTS

| 3,705,907 | 12/1972 | Troxler | 260/326.15 |
| 3,751,429 | 8/1973 | Seeman et al. | 260/326.15 |
| 3,808,231 | 4/1974 | Seeman et al. | 260/326.15 |
| 3,929,793 | 12/1975 | Popelak et al. | 544/373 |
| 4,076,829 | 2/1978 | Kampe et al. | 260/326.15 |
| 4,080,463 | 3/1978 | Troxler | 260/326.15 |

FOREIGN PATENT DOCUMENTS 2337461 6/1975 Fed. Rep. of Germany .

*Primary Examiner*—Paul M. Coughlan, Jr.
*Attorney, Agent, or Firm*—Gerald D. Sharkin; Robert S. Honor

[57] ABSTRACT

The compounds of formula I

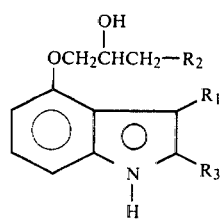

wherein
 $R_1$ is hydrogen or methyl,
 $R_3$ is hydrogen, methyl, hydroxymethyl, carboxyl, alkoxycarbonyl of 2 to 5 carbon atoms, carbamoyl or cyano and
 $R_2$ is a group (a) to (i), groups (a) to (i) having the following significances:

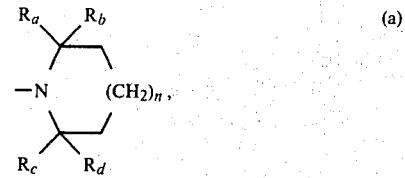

wherein n is 0 or 1 and $R_a$, $R_b$, $R_c$ and $R_d$ independently are hydrogen or alkyl of 1 to 4 carbon atoms;

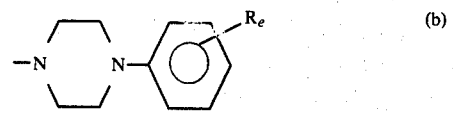

wherein $R_e$ is hydrogen or alkyl of 1 to 4 carbon atoms;

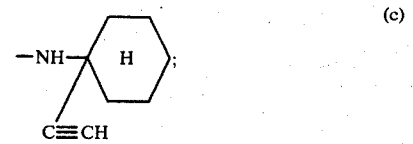

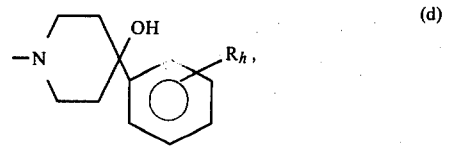

wherein $R_h$ is halogen of atomic number of from 9 to 35;

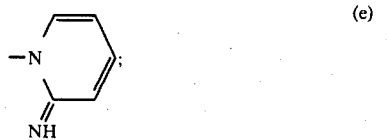

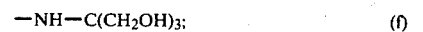

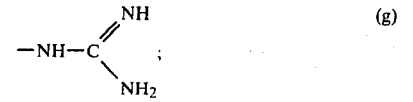

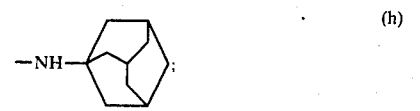

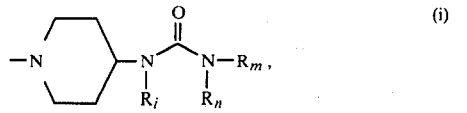

wherein
$R_i$ together with $R_n$ is o-phenylene optionally substituted by alkyl of 1 to 4 carbon atoms, alkoxy of 1 to 4 carbon atoms or halogen of atomic number of from 9 to 35 and,
when $R_3$ is cyano,
$R_i$ together with $R_n$ additionally is lower alkylene separating by 2 or 3 carbon atoms the nitrogen atom to which $R_i$ is bound from the nitrogen atom to which $R_n$ is bound and
$R_m$ is hydrogen or an aliphatic, cycloaliphatic, cycloaliphatic-aliphatic, araliphatic or aromatic moiety or an acyl moiety, with the provisos that,
(A) when $R_1$ is hydrogen and $R_2$ is a group (b), $R_3$ is methyl, hydroxymethyl, carbamoyl or cyano and
(B) when $R_2$ is a group (h), $R_3$ is hydrogen, carbamoyl or cyano.

The compounds are useful as antiarrhythmic, $\alpha$-adrenergic blocking and antihypertensive agents and, when a cyano or carbamoyl group is attached in the 2-position of the indole nucleus, additionally as $\beta$-adrenergic blocking agents.

8 Claims, No Drawings

3-AMINOPROPOXYARYL DERIVATIVES, THEIR PREPARATION AND PHARMACEUTICAL COMPOSITIONS CONTAINING THEM

The present invention relates to 3-aminopropoxyaryl derivatives, their preparation and pharmaceutical compositions containing them.

In accordance with the invention there are provided compounds of formula I

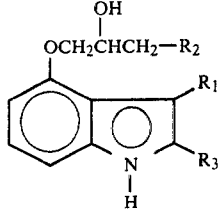

wherein
$R_1$ is hydrogen or methyl,
$R_3$ is hydrogen, methyl, hydroxymethyl, carboxyl, alkoxycarbonyl of 2 to 5 carbon atoms, carbamoyl or cyano and
$R_2$ is a group (a) to (i), groups (a) to (i) having the following significances:

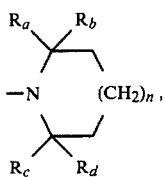

wherein n is 0 or 1 and $R_a$, $R_b$, $R_c$ and $R_d$ independently are hydrogen or alkyl of 1 to 4 carbon atoms;

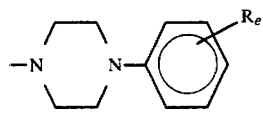

wherein $R_e$ is hydrogen or, alkyl of 1 to 4 carbon atoms;

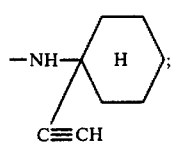

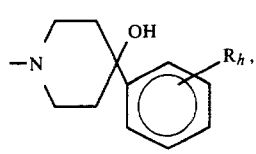

wherein $R_h$ is halogen of atomic number of from 9 to 35;

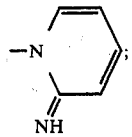

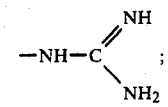

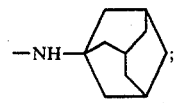

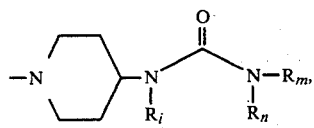

wherein
$R_i$ together with $R_n$ is o-phenylene optionally substituted by alkyl of 1 to 4 carbon atoms, alkoxy of 1 to 4 carbon atoms or halogen of atomic number of from 9 to 35 and,
when $R_3$ is cyano,
$R_i$ together with $R_n$ additionally is lower alkylene separating by 2 or 3 carbon atoms the nitrogen atom to which $R_i$ is bound from the nitrogen atom to which $R_n$ is bound and
$R_m$ is hydrogen or an aliphatic, cycloaliphatic, cycloaliphatic-aliphatic, araliphatic or aromatic moiety or an acyl moiety, with the provisos that,
(A) when $R_1$ is hydrogen and $R_2$ is a group (b), $R_3$ is methyl, hydroxymethyl, carbamoyl or cyano and
(B) when $R_2$ is a group (h), $R_3$ is hydrogen, carbamoyl or cyano, and physiologically acceptable hydrolyzable derivatives thereof having the hydroxy group in the 2 position of the 3-aminopropoxy side chain in esterified form.

A group of compounds of formula I are the compounds of formula Ipa

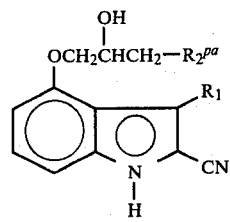

wherein
$R_1$ is as defined above and
$R_2{}^{pa}$ is a group (a), (b), (c) or (d), as defined above, or is a group ($i^{pa}$)

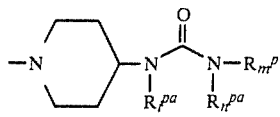 (i^{pa})

wherein
  $R_f{}^{pa}$ together with $R_n{}^{pa}$ is unsubstituted o-phenylene or alkylene of 2 or 3 carbon atoms and
  $R_m{}^p$ is hydrogen, alkyl of 1 to 4 carbon atoms or phenyl optionally mono- or disubstituted by alkyl of 1 to 4 carbon atoms, alkoxy of 1 to 4 carbon atoms or halogen of atomic number of from 9 to 35.
In a sub-group $R_2{}^{pa}$ is a group (i^{pa}).

Another group of compounds of formula I are the compounds of formula Ipb

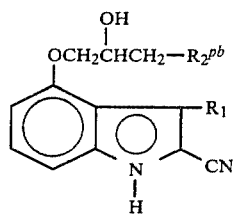 Ipb wherein
  $R_1$ is as defined above and
  $R_2{}^{pb}$ is a group (a), (b), (c), (e), (f), (g) or (h), as defined above, or is a group (i^{pb})

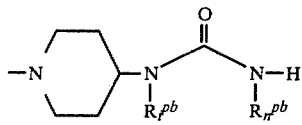 (i^{pb})

wherein
  $R_f{}^{pb}$ together with $R_n{}^{pb}$ is unsubstituted o-phenylene or ethylene.

In a sub-group $R_2{}^{pb}$ is a group (i^{pb}). In another sub-group $R_2{}^{pb}$ is a group (i^{pb}) wherein $R_f{}^{pb}$ together with $R_n{}^{pb}$ is unsubstituted o-phenylene.

Another group of compounds of formula I are the compounds of formula Ipc

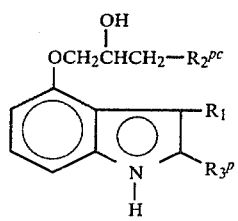 Ipc wherein
  $R_1$ is as defined above,
  $R_3{}^p$ is hydrogen, methyl, hydroxymethyl, carboxyl, alkoxycarbonyl of 2 to 5 carbon atoms or carbamoyl and
  $R_2{}^{pc}$ is a group (a), (b), (c) or (d), as defined above, or is a group (i^{pc})

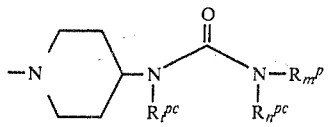 (i^{pc})

wherein
  $R_f{}^{pc}$ together with $R_n{}^{pc}$ is unsubstituted o-phenylene and
  $R_m{}^p$ is as defined above with the proviso that, when $R_1$ is hydrogen and $R_2{}^{pc}$ is a group (b), $R_3{}^p$ is methyl, hydroxymethyl or carbamoyl. In a sub-group $R_2{}^{pc}$ is a group (i^{pc}). In another sub-group $R_2{}^{pc}$ is as defined above with the proviso that, when $R_1$ is hydrogen and $R_2{}^{pc}$ is a group i^{pc}), $R_3{}^p$ is other than methyl.

Another group of compounds of formula I are the compounds of formula Ipd

Ipd wherein $R_1$, $R_2{}^{pb}$ and $R_3{}^p$ are as defined above, with the provisos that,
  (A') when $R_1$ is hydrogen and $R_2{}^{pb}$ is a group (b), $R_3{}^p$ is methyl, hydroxymethyl or carbamoyl and
  (B') when $R_2{}^{pb}$ is a group (h), $R_3{}^p$ is hydrogen or carbamoyl, and
  (C') when $R_2{}^{pb}$ is a group (i^{pb}), $R_f{}^{pb}$ together with $R_n{}^{pb}$ is unsubstituted o-phenylene.

In a sub-group $R_1$ is hydrogen and $R_3{}^p$ is chosen from hydrogen, methyl, carbamoyl, ethoxycarbonyl or isopropoxycarbonyl. In another sub-group $R_2{}^{pb}$ is a group (i^{pb}). In another sub-group $R_2{}^{pb}$ is as defined above for formula I^{pd} including the provisos, with the additional proviso that, when $R_1$ is hydrogen and $R_2{}^{pb}$ is a group (i^{pb}), $R_3{}^p$ is other than methyl.

A group of compounds of formula I are the compounds of formula Ia

Ia wherein
  $R_1$ and $R_3$ are as defined above and
  $R_2{}^a$ is a group (a) to (e), (g) or (h), as defined above, with provisos (A) and (B), as defined above when applied to $R_2$, and physiologically acceptable hydrolyzable derivatives thereof having the hydroxy group in the 2 position of the 3-aminopropoxy side chain in esterified form.

Another group of compounds of formula I are the compounds of formula Ib

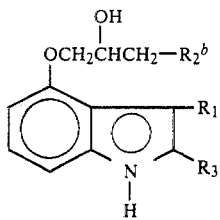

Ib wherein
R₁ and R₃ are as defined above and
R₂$^b$ is a group (f) or (i), as defined above, and physiologically acceptable hydrolyzable derivatives thereof having the hydroxy group in the 2 position of the 3-aminopropoxy side chain in esterified form.

In one sub-group R₂$^b$ is a group (i). In another sub-group R$_m$ is aromatic. In another sub-group R$_m$ is other than aromatic. In another sub-group R$_m$ is other than hydrogen, alkyl.

A preferred group of compounds of formula Ib are the compounds of formula Iba

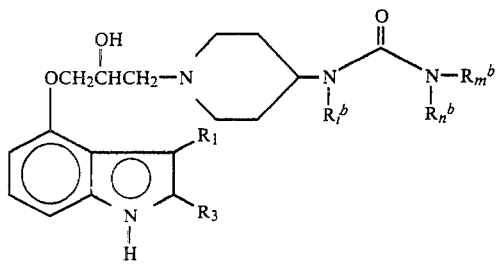

Iba wherein
R₁ and R₃ are as defined above,
R$_i^b$ together with R$_n^b$ is o-phenylene optionally mono- or disubstituted by alkyl of 1 to 4 carbon atoms, alkoxy of 1 to 4 carbon atoms or halogen of atomic number of from 9 to 35 and,
when R₃ is cyano,
R$_i^b$ together with R$_n^b$ additionally is alkylene of 2 or 3 carbon atoms separating by 2 or 3 carbon atoms the nitrogen atom to which R$_i^b$ is bound from the nitrogen atom to which R$_n^b$ is bound and
R$_m^b$ is hydrogen, alkyl of 1 to 4 carbon atoms or phenyl optionally mono-or disubstituted by alkyl of 1 to 4 carbon atoms, alkoxy of 1 to 4 carbon atoms or halogen of atomic number of from 9 to 35, and physiologically acceptable hydrolyzable derivatives thereof having the hydroxy group in the 2 position of the 3-aminopropoxy side chain in esterified form.

In a sub-group R₃ is other than methyl when R₁ is hydrogen.

Physiologically hydrolyzable derivatives are those derivatives which under physiological conditions are split to the corresponding compounds having a hydroxy group in the 2 position of the 3-aminopropoxy side chain.

A group of derivatives in esterified form of the compounds of formula I are e.g. the compounds of formula E

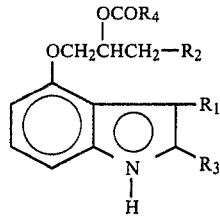

E wherein
R₁ to R₃ are as defined above, including provisos (A) and (B), and
R₄ is alkyl of 1 to 12 carbon atoms, cycloalkyl of 3 to 7 carbon atoms, phenyl, phenylalkyl of 7 to 12 carbon atoms, phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

Groups of derivatives in esterified form of the compounds of formula Ia, Ib and Iba are the corresponding derivatives, wherein R₄ has the significance indicated above.

Preferred are the compounds wherein the hydroxy group in the 2 position of the 3-aminopropoxy side chain is in free form.

R₁ preferably is hydrogen, R₃ preferably is carboxyl or cyano, especially cyano. R₂ preferably is a group (a), (b), (d) or (i), preferably (b), (d), or (i) and especially (i). R$_a$, R$_b$, R$_c$ and R$_d$ preferably are alkyl. They are preferably identical. When they are not identical, one of R$_a$ and R$_b$ and one of R$_c$ and R$_d$ preferably are hydrogen. R$_e$ preferably is alkyl. It is preferably in the o- or p-, and especially in the o-position. R$_h$ preferably is in the p-position. R$_i$ together with R$_n$ preferably is o-phenylene as defined above. When o-phenylene is substituted, it preferably is mono- or di-, especially monosubstituted. When it is monosubstituted, the substituent conveniently is in the para position to either of the nitrogen atoms. When it is disubstituted, each of the substituents is conveniently para to the nitrogen atoms. When it is substituted, it conveniently is substituted by halogen. When it is polysubstituted, the substituents are preferably identical. R$_m$ preferably is hydrogen or an aliphatic, araliphatic or aromatic moiety, especially hydrogen or an aliphatic or aromatic moiety, e.g. R$_m^p$ as defined above, and especially hydrogen. When R$_m$ is or contains an aliphatic moiety, it may for example be an alkyl radical having a carbon chain of up to 10 carbon atoms. The alkyl radical may for example be substituted e.g. by hydroxy, alkoxy, alkanoyloxy, alkylthio, mercapto or halogen, as in hydroxyethyl. When R$_m$ is an araliphatic radical it may be for example optionally substituted benzyl or phenylethyl. Cycloalkyl and cycloaliphatic aliphatic may for example have a carbon ring of 3 to 8 carbon atoms. Acyl may be alkanoyl or alkoxycarbonyl. An aromatic radical is for example an optionally substituted phenyl radical. When R$_m$ is optionally substituted phenyl, it is preferably unsubstituted phenyl or mono- or disubstituted phenyl. When it is monosubstituted, the substituent conveniently is in the para-position. When it is disubstituted, the substituents conveniently are in the ortho or para positions. When it is polysubstituted, the substituents preferably are identical. It is conveniently substituted by halogen or alkoxy, and especially halogen. $R_4$ preferably is alkyl or phenyl. Alternatively, $R_4$ conveniently is cycloalkyl, substituted phenyl or substituted or unsubstituted phenylalkyl.

Alkyl (except as indicated herein under for $R_4$), alkylthio and/or alkoxy preferably are of 1 or 2, especially 1 carbon atom. Alkoxycarbonyl or alkanoyl preferably is of 2 or 3, especially 2 carbon atoms. When it is of more than 3 carbon atoms, it is preferably branched in the position $\alpha$ to the carbonyl moiety, as in isopropoxycarbonyl. n preferably is 0. Halogen preferably is chlorine or bromine, especially chlorine. Lower alkylene preferably is of 2 to 7, especially 2 or 3, especially 2 carbon atoms. When it is of 3 carbon atoms it is preferably trimethylene.

When $R_4$ is alkyl, it is preferably of 3 to 5 carbon atoms and preferably is branched, especially in the position $\alpha$ to the carbonyl group to which it is bound, as e.g. in isopropyl, tert-butyl and 3-pentyl, and especially tert-butyl. Cycloalkyl preferably is of 5 or 6 carbon atoms. When $R_4$ is monosubstituted phenyl or phenylalkyl, the substituent preferably is in the p-position. When $R_4$ is di- or trisubstituted phenyl or phenylalkyl, the substituents preferably are in the meta and para positions. When $R_4$ is di- or trisubstituted, the substituents preferably are identical.

In accordance with the invention, a compound of the invention may be obtained by a process comprising reacting a corresponding compound of formula II

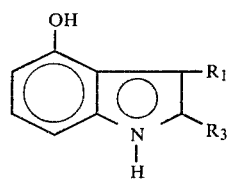

wherein $R_1$ and $R_3$ are as defined above, and $R_x$ is a group capable of reacting with a primary or secondary amine to give a 2-amino-1-hydroxyethyl group, with an appropriate compound of formula III $R_2$—H          III wherein $R_2$ is as defined above, and, where required, appropriately esterifying the 2 position of the 3-aminopropoxy side chain in the resulting compound of formula I.

The amination process may be effected in conventional manner for the production of analogous 3-amino-2-hydroxypropoxyaryl compounds. For example $R_x$ may be a group of formula

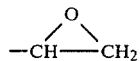

or a derivative of this group, e.g. a group of formula —CH(OH)—CH$_2$Y, wherein Y is chlorine, bromine or a group $R_y$—SO$_2$—O—, wherein $R_y$ is phenyl, tolyl or lower alkyl. Y is especially chlorine. The reaction is preferably effected in isopropanol or in an appropriate ether such as dioxane. Optionally an excess of the amine may be used as solvent. Alternatively the reaction may be effected in a fusion melt. Suitable reaction temperatures may be from about 20° to about 200° C., conveniently the reflux temperature of the reaction mixture when a solvent is present.

The optional substitution of the 2-hydroxy group in the side chain may be effected in conventional manner. For example, it may be esterified in manner known for the production of analogous esters of 3-amino-2-hydroxypropoxyaryl compounds, if necessary using selective reactions when other reactive groups are present. When $R_3$ is hydroxymethyl or carbamoyl, or when $R_2$ is a group (d) or (f), such esterification step is effected selevtively in the 2 position of the 3-aminopropoxy side chain, conveniently under temporary protection of the other reactive group or groups that may be present, e.g. for hydroxy in the form of e.g. a benzyloxy group, and subsequent selective splitting of the protecting group, e.g. by hydrogenation.

Free base forms of the compounds of the invention may be converted into salt forms in conventional manner and vice versa. Suitable acids for acid addition salt formation include maleic, malonic and fumaric acid. When $R_3$ is carboxyl, salts may also be formed with strong bases, e.g. sodium hydroxide.

In the compounds of the invention, the carbon atom in e.g. the 2 position of the 3-aminopropoxy side chain is asymmetrically substituted. The compounds may thus exist in the racemic form or in individual optical isomer form. The preferred optical isomer has the S configuration at this asymmetrically substituted carbon atom of the 3-aminopropoxy side chain.

Individual optical isomer forms may be obtained in conventional manner, for example by using optically active starting materials or by fractional crystallisation using optically active acids.

A compound used as a starting material may be obtained in conventional manner.

In particular, a compound of formula II may be obtained by introducing by O-alkylation a group —OCH$_2$—R$_x$ into a compound of formula IV wherein $R_1$ and $R_2$ are as defined above. The compounds of formula IV are preferably reacted in anionic form.

4-Hydroxy-1H-indole-2-carbonitrile and 4-Hydroxy-3-methyl-1H-indole-2-carbonitrile may be obtained by splitting off of a water molecule from the corresponding 2-carboxamide derivative, e.g. using titanium tetrachloride.

4-(2,3-Epoxypropoxy)-1H-indole-2-carbonitrile and 4-(2,3-epoxypropoxy)-3-methyl-1H-indole-2-carbonitrile may e.g. also be obtained from the corresponding 2-carboxamide derivative, e.g. using trifluoro-acetic acid anhydride.

Insofar as the preparation of any particular starting material is not particularly described, this may be effected in conventional manner.

In the following examples all temperatures are in degrees Centigrade and are uncorrected.

EXAMPLE 1

4-{3-[4-(1,2-dihydro-2-oxobenzimidazol-1-yl)piperidin-1-yl]-2-hydroxypropoxy}-1H-indole-2-carbonitrile A mixture of 10 g of 4-(2,3-epoxypropoxy)-1H-indole-2-carbonitrile and 10.18 g 1-(4-piperidinyl)benzimidazol-2(3H)-on in 150 ml dioxane are heated 20 hours under reflux. The reaction mixture is then cooled off, treated with active charcoal and filtered. The solution is concentrated and crystallization induced by the addition of ethanol (M.P. of the title compound 228°–230° after recrystallization from tetrahydrofuran/methylene chloride; M.P. of the hydrogen malonate of the title compound 199°[dec.]).

The starting material is obtained as follows: 7 g 4-(2,3-epoxypropoxy)-1H-indole-2-carboxamide, 90 ml dioxane and 7.2 g pyridine are cooled under stirring to 10°. 10.45 g trifluoroacetic anhydride dissolved in 45 ml dioxane are then slowly added, the temperature being maintained at 10°–12°. After 2 hours further stirring at room temperature, 500 ml methylene chloride are added, the solution is agitated and decanted twice with 300 ml water and the organic phase dried over magnesium sulphate. The violet solution is then filtered over talc and the solvent evaporated. The viscous liquid residue is chromatographed over 200 g silica gel (Merck Art. 7733), using methylene chloride having 1% methanol as an eluant. The pure fractions are dissolved in methylene chloride/methanol, the solution is concentrated and ether added. The crystals formed are filtered off, washed with ether and dried at 60° under vacuum (M.P. of 4-(2,3-epoxypropoxy)-1H-indole-2-carbonitrile: 149°–151°).

From the appropriate compound of formula II, wherein $R_x$ is

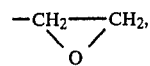

the following compounds of formula I may be obtained by reaction with the appropriate compound of formula III in analogous manner to Example 1:

| Example No. | $R_1$ | $R_3$ | $R_2$ | | M.P. |
|---|---|---|---|---|---|
| Group (a) | | | | | |
| 2 | H | CN | piperidine with Me,Me,Me,Me | | 180–182° |
| 3 | H | COOEt | piperidine with Me,Me,Me,Me | | 145–146° |
| 4 | H | Me | piperidine with Me,Me,Me,Me | | 107–109° |
| 5 | H | H | piperidine with Me,Me,Me,Me | fu | 231–233° |
| 6 | H | CONH$_2$ | piperidine with Me,Me,Me,Me | ch | 170–172° |
| 7 | H | Me | piperidine with Me,Me,Me,Me | fu | 204–206° |
| Group (b) | | | | | |
| 8 | H | CN | -N(piperazine)N-phenyl(Me) | | 178–180° |

-continued

| Example No. | R₁ | R₃ | R₂ | | M.P. |
|---|---|---|---|---|---|
| 9 | H | CONH₂ | -N(piperazinyl)-N-(2-methylphenyl) | | 201–203° |
| Group (c) | | | | | |
| 10 | H | CN | -NH-(cyclohexyl-C≡CH) | ch | 218° (dec.) |
| 11 | H | Me | -NH-(cyclohexyl-C≡CH) | hfu | 108–110° |
| 12 | H | H | -NH-(cyclohexyl-C≡CH) | | 154–156° |
| Group (d) | | | | | |
| 13 | H | CN | -N(piperidinyl with 4-chlorophenyl and OH) | hfu | 189° (dec.) |
| Group (e) | | | | | |
| 14 | H | H | -N(tetrahydropyridinyl=NH) | | 170–171° |
| Group (f) | | | | | |
| 15 | H | CONH₂ | -NH-C(CH₂OH)₃ | | 190–193° |
| 16 | H | H | -NH-C(CH₂OH)₃ | | 144–145° |
| 17 | H | COOiPr | -NH-C(CH₂OH)₃ | | 171–173° |
| 18 | H | Me | -NH-C(CH₂OH)₃ | | 142–144° |
| 19 | H | CN | -NH-C(CH₂OH)₃ | | |
| 20 | Me | CN | -NH-C(CH₂OH)₃ | | |
| Group (g) | | | | | |
| 21 | H | H | -NH-C(NH)NH₂ | nd | 230° (dec.) |
| Group (h) | | | | | |
| 22 | H | H | 1-adamantyl-amino | | 99–101° |
| Group (i) | | | | | |
| 23 | H | H | -N(piperidinyl-benzimidazol-2-one) | | 210–212° |
| 24 | H | Me | -N(piperidinyl-benzimidazol-2-one) | | 167° |
| 25 | Me | CN | -N(piperidinyl-benzimidazol-2-one) | ch | 261° (dec.) |
| 26 | H | CN | -N(piperidinyl-N-methyl-benzimidazol-2-one) | | |

-continued
| Example No. | R₁ | R₃ | R₂ | M.P. |
|---|---|---|---|---|
| 27 | H | CN | 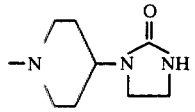 | 212–214° |
| 28 | H | CN | 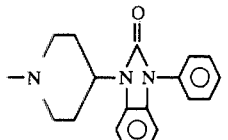 | |
| 29 | H | CN | 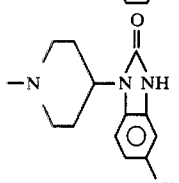 | |
| 30 | H | CN | 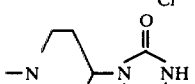 | |
| 31 | H | CN | 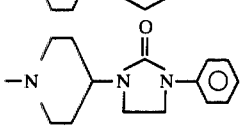 | |
| 32 | Me | CN | 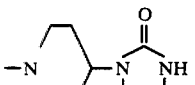 | |
| 33 | H | CH₂OH | 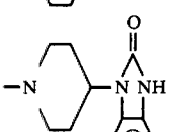 | |
| 34 | H | CONH₂ | 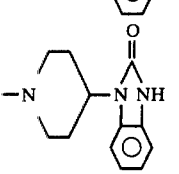 | |
ch = hydrochloride
fu = bis[base]fumarate
hfu = hydrogen fumarate
nd = bis[base]naphthalene-1,5-disulfonate
Me = methyl
Et = ethyl
iPr = isopropyl
The following compounds of formula I may also be obtained in a manner analogous to Example 1:
| Example | R₁ | R₃ | R₂ |
|---|---|---|---|
| Group (a) | | | |
| 35 | Me | COOH | 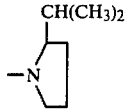 |
| 36 | Me | CN | 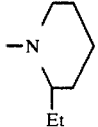 |

-continued

| Example | R₁ | R₃ | R₂ |
|---|---|---|---|
| 37 | Me | CH₂OH | 2,6-diethylpiperidin-1-yl |

Group (b)

| Example | R₁ | R₃ | R₂ |
|---|---|---|---|
| 38 | Me | COO(CH₂)₂CH₃ | 4-phenylpiperazin-1-yl |
| 39 | Me | Me | 4-(4-tert-butylphenyl)piperazin-1-yl |
| 40 | H | Me | 4-(2-isopropylpyridin-... )piperazin-1-yl |

Group (c)

| Example | R₁ | R₃ | R₂ |
|---|---|---|---|
| 42 | Me | CH₂OH | —NH—CH(C≡CH)(cyclohexyl) |
| 43 | Me | COOH | —NH—CH(C≡CH)(cyclohexyl) |
| 44 | H | COO(CH₂)₂CH₃ | —NH—CH(C≡CH)(cyclohexyl) |
| 45 | Me | CONH₂ | —NH—CH(C≡CH)(cyclohexyl) |

Group (d)

| Example | R₁ | R₃ | R₂ |
|---|---|---|---|
| 46 | Me | COO(CH₂)₂CH₃ | 4-hydroxy-4-(3-fluorophenyl)piperidin-1-yl |
| 47 | Me | CONH₂ | 4-hydroxy-4-(3-bromophenyl)piperidin-1-yl |

Group (e)

| Example | R₁ | R₃ | R₂ |
|---|---|---|---|
| 48 | Me | CN | 2-imino-pyridin-1-yl |

Group (f)

| Example | R₁ | R₃ | R₂ |
|---|---|---|---|
| 49 | Me | COOH | —NH—C(CH₂OH)₃ |
| 50 | Me | CH₂OH | —NH—C(CH₂OH)₃ |

Group (i)

| Example | R₁ | R₃ | R₂ |
|---|---|---|---|
| 51 | Me | CN | 4-[3-(4-fluorophenyl)-6-fluoro-2-oxo-2,3-dihydrobenzimidazol-1-yl]piperidin-1-yl |

-continued

| Example | R₁ | R₃ | R₂ |
|---|---|---|---|
| 52 | Me | CN | 1-(4-piperidyl)-3-phenyl-4-ethyl-6-methoxy-benzimidazol-2(3H)-one |
| 53 | Me | CN | 1-(4-piperidyl)-3-isopropyl-5-methyl-6-bromo-benzimidazol-2(3H)-one |
| 54 | H | CN | 1-(4-piperidyl)-3-(3-chloro-4-bromophenyl)-tetrahydropyrimidin-2(1H)-one |
| 55 | Me | CN | 1-(4-piperidyl)-3-(3-methoxy-4-ethoxyphenyl)-4-methyl-imidazolidin-2-one |
| 56 | Me | CN | 1-(4-piperidyl)-3-(2-methyl-4-isopropylphenyl)-5,6-dibromo-benzimidazol-2(3H)-one |
| 57 | Me | CN | 1-(4-piperidyl)-4-methoxy-7-propoxy-benzimidazol-2(3H)-one (NH) |
| 58 | Me | CH₂OH | 1-(4-piperidyl)-3-(2-bromo-4-methoxyphenyl)-7-bromo-benzimidazol-2(3H)-one |
| 59 | Me | COOH | 1-(4-piperidyl)-3-(4-fluorophenyl)-4-ethoxy-6-chloro-benzimidazol-2(3H)-one |
| 60 | H | COOEt | 1-(4-piperidyl)-3-n-butyl-benzimidazol-2(3H)-one |
| 61 | H | CONH₂ | 1-(4-piperidyl)-3-(2,6-dimethylphenyl)-5,6-diethyl-benzimidazol-2(3H)-one |
| 62 | Me | CN | 1-(4-piperidyl)-3-cyclopentyl-4-methyl-imidazolidin-2-one |

-continued

| Example | R₁ | R₃ | R₂ |
|---|---|---|---|
| 63 | Me | CN | (structure: piperidinyl-N-benzimidazolone with OEt substituent and N-CH₂-cyclopropyl) |
| 64 | H | CN | (structure: piperidinyl-N-benzimidazolone with two Cl substituents and N-CH₂-(3-bromophenyl)) |
| 65 | Me | CONH₂ | (structure: piperidinyl-N-benzimidazolone with Et substituent and N-cyclohexyl) |
| 66 | Me | COOC(CH₃)₃ | (structure: piperidinyl-N-benzimidazolone with Cl and Br substituents and N-(CH₂)₃-cyclopentyl) |
| 67 | Me | COOH | (structure: piperidinyl-N-benzimidazolone with two OEt substituents and N-(CH₂)₃-(2-fluoro-5-chlorophenyl)) |
| 68 | H | CH₂OH | (structure: piperidinyl-N-benzimidazolone with two Me substituents and N-(4-ethylphenyl)) |

The following derivatives, esters of the compounds of formula I (which are compounds of formula E) may be obtained by appropriately esterifying the 2 position of the 3-aminopropoxy side chain in the corresponding compounds of formula I (R₁, R₂ and R₃ are as for the corresponding compound of formula I):

| Example No. | Corresponding compound of formula I (Example No.) | R₄ |
|---|---|---|
| Group (a) | | |
| 2E | 2 | n-nonyl |
| 3E | 3 | ethyl |
| 5E | 5 | 3-ethylbenzyl |
| 6E | 6 | 3-methyl-4-(3,4,5-triethoxy-phenyl)butyl |
| 7E1 | 7 | cyclobutyl |
| 7E2 | 7 | cycloheptyl |
| 35E | 35 | 2-fluoro-3-chlorophenyl |
| 37E | 37 | 5-phenylpentyl |
| Group (b) | | |
| 8E1 | 8 | n-nonyl |
| 8E2 | 8 | ethyl |
| 38E | 38 | 3-ethylbenzyl |
| 39E1 | 39 | 3-methyl-4-(3,4,5-triethoxy-phenyl)butyl |

-continued

| Example No. | Corresponding compound of formula I (Example No.) | R₄ |
|---|---|---|
| 39E2 | 39 | cyclobutyl |
| 39E3 | 39 | cycloheptyl |
| 40E | 40 | 2-fluoro-3-chlorophenyl |
| 41E | 41 | 5-phenylpentyl |
| Group (c) | | |
| 42E1 | 42 | n-nonyl |
| 42E2 | 42 | ethyl |
| 42E3 | 42 | 3-ethylbenzyl |
| 44E1 | 44 | 3-methyl-4-(3,4,5-triethoxy-phenyl)butyl |
| 44E2 | 44 | cyclobutyl |
| 44E3 | 44 | cycloheptyl |
| 44E4 | 44 | 2-fluoro-3-chlorophenyl |
| 45E | 45 | 5-phenylpentyl |
| Group (f) | | |
| 15E | 15 | n-nonyl |
| 16E | 16 | ethyl |
| 18E | 18 | 3-ethylbenzyl |
| 20E1 | 20 | 3-methyl-4-(3,4,5-triethoxy-phenyl)butyl |
| 20E2 | 20 | cyclobutyl |
| 49E | 49 | cycloheptyl |
| 50E1 | 50 | 2-fluoro-3-chlorophenyl |

-continued

| Example No. | Corresponding compound of formula I (Example No.) | R$_4$ |
|---|---|---|
| 50E2 | 50 | 5-phenylpentyl |
| Group (g) | | |
| 21E1 | 21 | n-nonyl |
| 21E2 | 21 | ethyl |
| 21E3 | 21 | 3-ethylbenzyl |
| 21E4 | 21 | 3-methyl-4-(3,4,5-triethoxy-phenyl)butyl |
| 21E5 | 21 | cyclobutyl |
| 21E6 | 21 | cycloheptyl |
| 21E7 | 21 | 2-fluoro-3-chlorophenyl |
| 21E8 | 21 | 5-phenylpentyl |
| Group (h) | | |
| 22E1 | 22 | n-nonyl |
| 22E2 | 22 | ethyl |
| 22E3 | 22 | 3-ethylbenzyl |
| 22E4 | 22 | 3-methyl-4-(3,4,5-triethoxy-phenyl)butyl |
| 22E5 | 22 | cyclobutyl |
| 22E6 | 22 | cycloheptyl |
| 22E7 | 22 | 2-fluoro-3-chlorophenyl |
| 22E8 | 22 | 5-phenylpentyl |
| Group (i) | | |
| 23E | 23 | n-nonyl |
| 24E | 24 | ethyl |
| 25E | 25 | 3-ethylbenzyl |
| 27E | 27 | 3-methyl-4-(3,4,5-triethoxy-phenyl)butyl |
| 52E | 52 | cyclobutyl |
| 55E | 55 | cycloheptyl |
| 59E | 59 | 2-fluoro-3-chlorophenyl |
| 61E | 61 | 5-phenylpentyl |

The compounds of the invention are useful because they exhibit pharmacological activity in animals.

The compounds exhibit antiarrhythmic activity, as indicated in standard tests. For example, they prolong the functional refractory period in the left guinea pig atrium at a concentration of from $10^{-6}$ to $10^{-4}$ M of the compounds in accordance with the principles of N. Reuter and E. Heeg [Arch. Pharmakol. 268 (1971) 323-333].

The compounds are therefore useful as antiarrhythmic agents, e.g. for the treatment of heart rhythm disorders such as heart flutter.

Preferred in this indication are the compounds wherein R$_2$ is a group (a) to (e), (g) and (h), especially (a), (b), (d) or (e).

The compounds also exhibit α-adrenergic blocking activity, as indicated by standard tests. For example, the inhibition of α-adrenoceptors may be observed in isolated spiral strips of the Vena femoralis of dogs (E. Müller-Schweinitzer and E. Stürmer, Br. J. Pharmacol. [1974] 51, 441-446) at a bath concentration of from about $10^{-7}$ M to about $10^{-5}$ M.

The compounds are therefore useful as α-adrenergic blocking agents, e.g. for the prophylaxis and treatment of disorders related to a paralysis of intestine motility, such as paralytic ileus.

Preferred in this indication are the compounds wherein R$_2$ is a group (i), especially the compounds of Examples 1,23 and 24, especially Example 1.

The compounds also exhibit antihypertensive activity, as indicated in standard tests. For example, in the Grollman rat test [A. Grollman, Proc. Soc. Exp. Biol. and Med. 57 (1944) 102] on i.v. and s.c. administration of from 0.1 to 10 mg/kg animal body weight of the compounds, and on p.o. administration of from 10 to 100 mg/kg.

The compounds are therefore useful as antihypertensive agents.

Preferred in this indication are the compounds wherein R$_3$ is other than methyl, and R$_2$ is a group (a), (f) or (i), especially a group (i), especially the compounds of Example 1 and 23, and especially Example 1.

The compounds having a cyano or carbamoyl group in the 2 position of the indole ring, especially a cyano group, possesses β-adrenergic blocking activity, as indicated by standard tests. For example, in the isolated, spontaneously-beating guinea pig atrium (method of K. Saameli, Helv. Physiol. Acta 25 [1967] CR 219-CR 221) inhibition of the positive inotropic effect of adrenaline is observed at a bath concentration of about $10^{-9}$ M to about $10^{-6}$ M.

These compounds are therefore useful as β-adrenergic blocking agents, e.g. for the prophylaxis and treatment of coronary diseases such as Angina pectoris, of conditions resulting from sympathetic overstimulation, such as nervous heart ailments, of myocardial infarct, for interval migraine treatment, and for the treatment of glaucoma and thyreotoxicosis.

Preferred in this indication are the compounds of Examples 1, 24 and 25, especially Example 1.

It will be appreciated that it may be necessary to convert a compound having a substituted hydroxy group in the 2 position of the 3-aminopropoxy side chain to the corresponding free hydroxy compound prior to carrying out the tests indicated above for showing α- and β-adrenergic blocking activity.

The compounds of formula Ib exhibit more beneficial properties than would be expected for compounds of this type, for example, beta-blockade in the case of the 2-cyano or 2-carbamoyl compounds wherein R$_2^b$ is a group (i), especially the 2-cyano compounds, freedom from undesirable side effects, long duration of activity, etc.

For the above-mentioned uses the dosage will, of course, vary depending on the compound employed, mode of administration and treatment desired. However, in general, satisfactory results are obtained when administered at a daily dosage of from about 0.01 mg to about 100 mg per kg animal body weight, conveniently given in divided doses 2 to 4 times a day or in sustained release form. For the larger mammals, the total daily dosage is in the range of from about 0.1 mg to about 1000 mg, and dosage forms suitable for oral administration comprise from about 0.25 mg to about 500 mg of the compounds admixed with a solid or liquid pharmaceutical carrier or diluent. Examples of daily doses are from 0.1 to 100 mg, from 5 to 50 mg and from 1 to 1000 mg.

In general, the 2(S) optical isomers of the compounds are more active than the 2 (R) optical isomers as β-blocking agents.

The compounds may be administered in pharmaceutically acceptable salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be in the form of, for example, a tablet.

In a 1st group of compounds R$_1$ is hydrogen.
In a 1st group of compounds R$_1$ is methyl.

In a 3rd group of compounds $R_3$ is hydrogen.
In a 4th group of compounds $R_3$ is methyl.
In a 5th group of compounds $R_3$ is hydroxymethyl.
In a 6th group of compounds $R_3$ is carboxyl.
In a 7th group of compounds $R_3$ is alkoxycarbonyl.
In a 8th group of compounds $R_3$ is carbamoyl.
In a 9th group of compounds $R_3$ is cyano.
In a 10th group of compounds $R_2$ is a group (a), wherein n is 0.
In an 11th group of compounds $R_2$ is a group (a), wherein n is 1.
In a 12th group of compounds $R_2$ is a group (b).
In a 13th group of compounds $R_2$ is a group (c).
In a 14th group of compounds $R_2$ is a group (d).
In a 15th group of compounds $R_2$ is a group (e).
In a 16th group of compounds $R_2$ is a group (f).
In a 17th group of compounds $R_2$ is a group (g).
In an 18th group of compounds $R_2$ is a group (h).
In a 19th group of compounds $R_2$ is a group (i), wherein $R_i$ together with $R_n$ is o-phenylene optionally substituted as stated above.
In a 20th group of compounds $R_2$ is a group (i), wherein $R_i$ together with $R_n$ is lower alkylene.
In a 21st group of compounds $R_2$ is a group (i), wherein $R_i$ together with $R_n$ is unsubstituted phenylene.
In a 22nd group of compounds $R_m$ is hydrogen.
In a 23rd group of compounds $R_m$ is aliphatic.
In a 24th group of compounds $R_m$ is cycloaliphatic.
In a 25th group of compounds $R_m$ is cycloaliphaticaliphatic.
In a 26th group of compounds $R_m$ is araliphatic.
In a 27th group of compounds $R_m$ is aromatic.
In a 28th group of compounds $R_m$ is aryl.
In a 29th group of compounds $R_m$ is alkyl.

I claim:

1. A compound having the formula Ipa

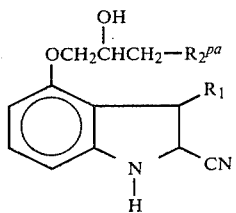

Ipa wherein
$R_1$ is hydrogen or methyl
$R_2{}^{pa}$ is a group (a), (b), (c) or (d), groups (a) to (d) having the following significances

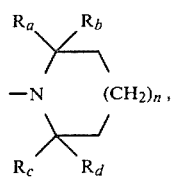

(a)

wherein n is 0 or 1 and $R_a$, $R_b$, $R_c$ and $R_d$ independently are hydrogen or alkyl of 1 to 4 carbon atoms;

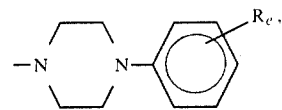

(b)

wherein $R_e$ is hydrogen or alkyl of 1 to 4 carbon atoms;

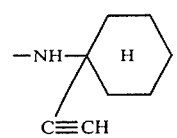

(c)

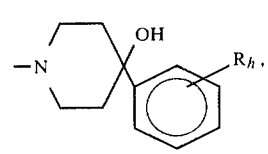

(d)

wherein $R_h$ is halogen of atomic number of from 9 to 35, or is a group ($i^{pa}$)

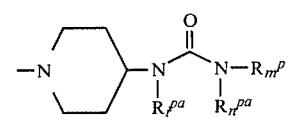

($i^{pa}$)

wherein
$R_i{}^{pa}$ together with $R_n{}^{pa}$ is unsubstituted o-phenylene or alkylene of 2 or 3 carbon atoms and
$R_m{}^p$ is hydrogen, alkyl of 1 to 4 carbon atoms or phenyl optionally mono- or disubstituted by alkyl of 1 to 4 carbon atoms, alkoxy of 1 to 4 carbon atoms or halogen of atomic number of from 9 to 35.

2. A compound of claim 1 wherein $R_2{}^{pa}$ is a group $i^{pa}$).

3. A compound having the formula Ipb

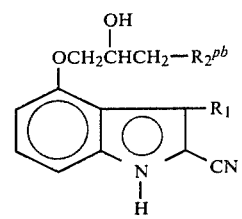

Ipb wherein
$R_1$ is hydrogen or methyl and
$R_2{}^{pb}$ is a group (a), (b), (c), (d), (e), (f), (g) or (h), groups (a) to (h) having the following significances

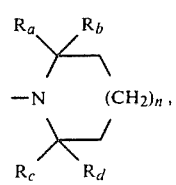

(a)

wherein n is 0 or 1 and $R_a$, $R_b$, $R_c$ and $R_d$ independently are hydrogen or alkyl of 1 to 4 carbon atoms;

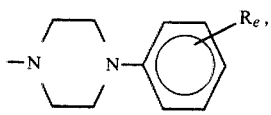 (b)

wherein $R_e$ is hydrogen or alkyl of 1 to 4 carbon atoms;

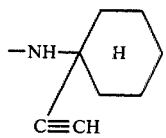 (c)

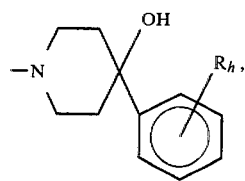 (d)

wherein $R_h$ is halogen of atomic number of from 9 to 35;

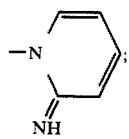 (e)

—NH—C(CH$_2$OH)$_3$; (f)

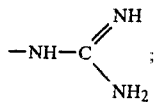 (g)

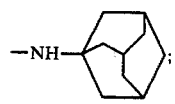 (h)

or is a group (i$^{pb}$)

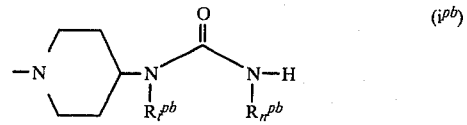 (i$^{pb}$)

wherein $R_f^{pb}$ together with $R_n^{pb}$ is unsubstituted o-phenylene or ethylene.

4. A compound of claim 3 wherein $R_2^{pb}$ is a group (i$^{pb}$).

5. A compound of claim 4 wherein $R_f^{pb}$ together with $R_n^{pb}$ is unsubstituted o-phenylene.

6. A compound having the formula E

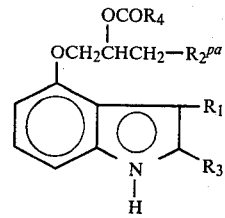 E wherein
$R_1$ is hydrogen or methyl,
$R_2^{pa}$ is as defined in claim 5,
$R_3$ is cyano, and
$R_4$ is alkyl of 1 to 12 carbon atoms, cycloalkyl of 3 to 7 carbon atoms, phenyl, phenylalkyl of 7 to 12 carbon atoms, phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms, or a pharmaceutically acceptable acid addition salt thereof.

7. A compound of claim 1 or 3 in pharmaceutically acceptable acid addition salt form.

8. A compound of claim 3 which is 4-{3-[4-(1,2-dihydro2-oxobenzimidazol-1-yl)piperidin-1-yl]-2-hydroxypropoxy}-1H-indole-2-carbonitrile, or a pharmaceutically acceptable salt thereof.

* * * * *